(12) United States Patent
Strauss et al.

(10) Patent No.: US 10,232,191 B2
(45) Date of Patent: *Mar. 19, 2019

(54) METHOD OF USE OF AN EMBOLIC IMPLANT FOR RADIO-ABLATIVE TREATMENT

(71) Applicant: Covidien LP, Mansfield, MA (US)

(72) Inventors: Brian M. Strauss, San Clemente, CA (US); Jeffrey J. Valko, San Clemente, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/635,258

(22) Filed: Jun. 28, 2017

(65) Prior Publication Data

US 2017/0296839 A1  Oct. 19, 2017

Related U.S. Application Data

(63) Continuation of application No. 14/261,285, filed on Apr. 24, 2014, now Pat. No. 9,694,201.

(51) Int. Cl.
| | | |
|---|---|---|
| *A61N 5/10* | (2006.01) | |
| *A61B 17/12* | (2006.01) | |
| *A61B 18/00* | (2006.01) | |
| *A61B 17/00* | (2006.01) | |

(52) U.S. Cl.
CPC ...... *A61N 5/1002* (2013.01); *A61B 17/12109* (2013.01); *A61B 17/12172* (2013.01); *A61B 17/12186* (2013.01); *A61B 18/00* (2013.01); *A61N 5/1007* (2013.01); *A61B 17/00491* (2013.01); *A61B 17/1219* (2013.01); *A61B 17/12177* (2013.01); *A61B 2017/00898* (2013.01); *A61B 2017/00942* (2013.01); *A61B 2018/00577* (2013.01); *A61N 2005/1021* (2013.01); *A61N 2005/1098* (2013.01)

(58) Field of Classification Search
CPC .......... A61N 2005/1021; A61N 5/1002; A61N 5/1007; A61N 2005/1098
See application file for complete search history.

(56) References Cited

U.S. PATENT DOCUMENTS

| | | | |
|---|---|---|---|
| 5,683,411 | A | 11/1997 | Kavteladze et al. |
| 5,755,773 | A | 5/1998 | Evans et al. |
| 5,951,599 | A | 9/1999 | McCrory |
| 7,118,592 | B1 | 10/2006 | Dang et al. |
| 8,641,777 | B2 | 2/2014 | Strauss et al. |

(Continued)

FOREIGN PATENT DOCUMENTS

| | | |
|---|---|---|
| EP | 0793457 B2 | 9/1997 |
| EP | 0915685 B1 | 5/1999 |

(Continued)

OTHER PUBLICATIONS

Geyik et al., "Neuroapplication of Amplatzer Vascular Plug: A Novel Device for Parent Artery Occlusion," Interventional Neuroradiology, Journal of Neuroradiology, Springer, Nov. 29, 2007, 5 pp.

(Continued)

*Primary Examiner* — Christine H Matthews
(74) *Attorney, Agent, or Firm* — Shumaker & Sieffert, P.A.

(57) ABSTRACT

A method of radio-ablation in conjunction with embolic implants used for pre-embolization of branch arteries in radio-ablation of the liver or other diseased tissue.

22 Claims, 15 Drawing Sheets

(56) References Cited

U.S. PATENT DOCUMENTS

| | | |
|---|---|---|
| 9,301,827 B2 | 4/2016 | Strauss et al. |
| 9,694,201 B2 | 7/2017 | Strauss et al. |
| 2001/0001806 A1 | 5/2001 | Turnlund |
| 2003/0045898 A1 | 3/2003 | Harrison et al. |
| 2003/0153943 A1 | 8/2003 | Michael et al. |
| 2003/0163192 A1 | 8/2003 | Wallace |
| 2003/0229366 A1 | 12/2003 | Reggie et al. |
| 2004/0068288 A1 | 4/2004 | Palmer et al. |
| 2004/0091421 A1 | 5/2004 | Aston |
| 2005/0192620 A1 | 9/2005 | Cully et al. |
| 2006/0015136 A1 | 1/2006 | Besselink |
| 2006/0241735 A1 | 10/2006 | Tockman et al. |
| 2007/0135826 A1 | 6/2007 | Zaver et al. |
| 2009/0099592 A1 | 4/2009 | Buiser et al. |
| 2009/0105644 A1 | 4/2009 | Leonard et al. |
| 2009/0287291 A1 | 11/2009 | Becking et al. |
| 2011/0022149 A1 | 1/2011 | Cox et al. |
| 2011/0054519 A1 | 3/2011 | Neuss |
| 2011/0071624 A1 | 3/2011 | Finch et al. |
| 2011/0160763 A1 | 6/2011 | Ferrera et al. |
| 2016/0192942 A1 | 7/2016 | Strauss et al. |

FOREIGN PATENT DOCUMENTS

| | | |
|---|---|---|
| WO | 9726939 A1 | 7/1997 |
| WO | 0072909 A1 | 12/2000 |
| WO | 03063732 A2 | 8/2003 |
| WO | 2010030993 A1 | 3/2010 |
| WO | 2012166804 A1 | 12/2012 |

OTHER PUBLICATIONS

Lopez-Benitez et al., "Protective Embolization of the Gastroduodenal Artery with a One-HydroCoil Technique in Radioembolization Procedures," Cardiovascular Interventional Radiology, vol. 36(1), Springer Online, Mar. 14, 2012, 6 pp.

Murthy et al., "Radioembolization of Yttrium-90 Microsperes for Hepatic Malignancy," Seminars Interventional Radiology, vol. 25(1), Mar. 2008, 10 pp.

Ross et al., "The Vascular Plug: A New Device for Parent Artery Occulsuion," AJNR AM J Neuroradiol, Feb. 2007, 2 pp.

Prosecution History from U.S. Appl. No. 14/261,285, dated Jun. 15, 2016 through Jun. 14, 2017, 79 pp.

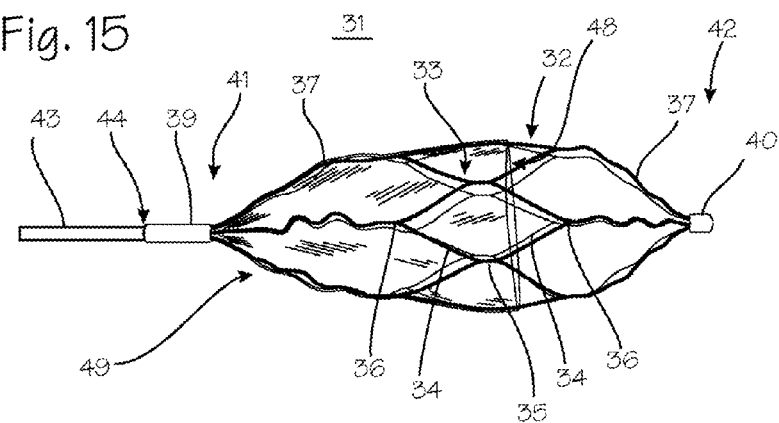
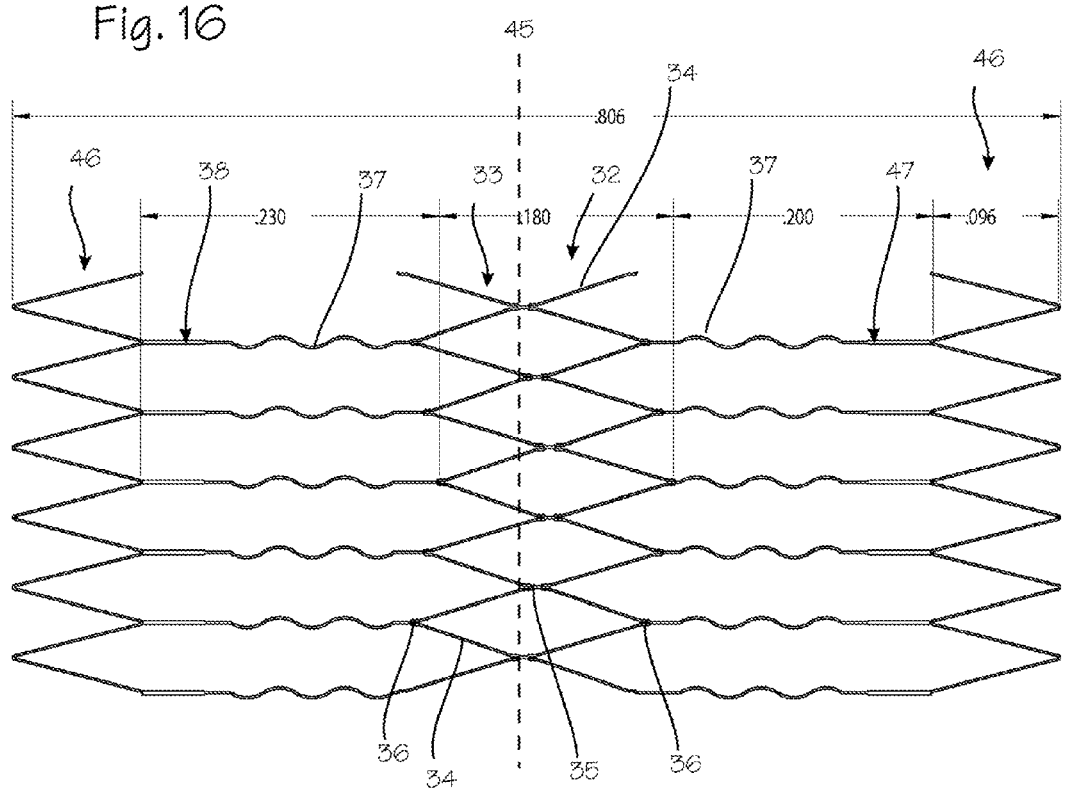

METHOD OF USE OF AN EMBOLIC IMPLANT FOR RADIO-ABLATIVE TREATMENT

This application is a continuation of U.S. patent application Ser. No. 14/261,285, filed Apr. 24, 2014, which will issue as U.S. Pat. No. 9,694,201 on Jul. 4, 2017, and is incorporated herein by reference in its entirety.

FIELD OF THE INVENTIONS

The inventions described below relate to the embolic implants for use in peripheral applications.

BACKGROUND OF THE INVENTIONS

Radio-embolization of the liver is used to treat cancer of the liver, and entails deposit of radioactive beads in the liver to kill cancer cells while leaving the bulk of the liver intact. The beads, or microspheres, contain Yttrium 90 (Y90), which is radioactive and emits ionizing radiation (beta radiation, which penetrates only slightly through body tissue). This radiation kills nearby tissue, including cancer cells and viable liver cells. The Y90 is thus deposited only near a malignant liver tumor. Y90 has a short half-life (2.67 days), so it decays away fairly quickly and will not harm other areas of the body or other parts of the liver unless themicrospheres used to deliver the Y90 flow immediately to unintended parts of the liver or the body.

To accomplish the therapy, a suspension of microspheres loaded with Yttrium 90 in a delivery fluid are injected by catheter into a blood vessel feeding the liver, or a small portion of the liver. The liver has a dual blood supply, being supplied with blood through the proper hepatic artery and the portal vein. The proper hepatic artery branches off the common hepatic artery, which in turn branches off the celiac artery which in turn branches off the aorta, to supply arterial blood to the liver. A catheter can be navigated to the proper hepatic artery and its branches starting through an access point in the femoral artery. The portal vein carries blood from the intestines to the liver. Radio-embolization of the liver is achieved through the hepatic artery, because it is easier to get to, and because most cancer in the liver is fed by the hepatic artery.

Radio-embolization entails deposition of numerous microspheres loaded with radioactive isotopes such as Y90. The microspheres cause blockage of the artery (embolization), with the effect of depriving cancerous regions of the liver of blood, while the beta radiation from the Y90 kills the cancerous cells. Though the hepatic artery is blocked, blood supply to the liver is provided through the portal vein, and the liver may quickly re-vascularize with new arteries arising from the hepatic artery and other nearby arteries.

In some cases, clinicians have taken to embolizing nearby extra-hepatic arteries, such as the arteries branching off the common or proper hepatic artery (gastroduodenal and supraduodenal arteries, for example), to prevent reflux of microspheres intended for the liver to unintended locations such as the intestines or spleen. The supraduodenal artery, for example, is proximal/upstream to the liver, so that the entire proper hepatic artery can be occluded with Y90 microspheres while protecting this artery. These upstream branch arteries are embolized with numerous coils or one large coil, deposited by catheter, through the same access pathway used to deliver the microsphere. This technique is demonstrated in Lopez-Benitez, *Protective Embolization of the Gastroduodenal Artery with a One-HydroCoil Technique in Radioembolization Procedures*, 36 Cardiovascular Interventional Radiology 105 (2013). As stated in this article, complete occlusion of the gastroduodenal artery can take over 30 minutes, and sometimes cannot be achieved. Since coil placement, flow monitoring to detect occlusion, and subsequent microsphere deposition are all visualized under fluoroscopy, the long time to accomplish occlusion thus represents a significant additional exposure to fluoroscopy for the patient and clinician, and a significant increase in the time to accomplish the radio-embolization procedure. The un-occluded length of the extra-hepatic artery not occluded by the coils can lead to recanalization and gastro-intestinal complications from radiation induced ulceration. Also, the coil implantation has not been effective in limiting recurrence and metastasis after trans-catheter arterial embolization.

In our prior U.S. patent, Strauss, et al., Embolic Implant And Method Of Use, U.S. Pat. No. 8,641,777, (Feb. 4, 2014) we disclosed an embolic implant for use in neurovascular applications. This implant provides immediate occlusion and stoppage of blood flow when deposited in a blood vessel. Though a summary of the devices disclosed is provided below, we incorporate by reference the entire disclosure U.S. Pat. No. 8,641,777.

The implant comprises a wire frame structure including a pair of opposing zigzag segments including a plurality of V-shaped elements defining an open end, with the V-shaped elements joined at the open end of the V-shaped elements via short longitudinally aligned struts to form a central portion of the wire-frame structure and a plurality of longitudinally oriented struts extending from the proximally pointing vertices of the V-shaped elements and joined together near the radial center of the wire-frame structure at the proximal end of the embolic implant. The wireframe structure is formed of a self-expanding material. A blood impermeable membrane is disposed over the one end of the embolic implant, and has a proximal facing surface, such that blood is substantially prevented from flowing through the implant when deployed in the parent artery.

The embolic implant can be used to improve a radio-ablation of the liver.

SUMMARY OF THE INVENTIONS

The devices and methods described below provide for radio-ablative treatment of the liver which more finely targets diseased regions of the liver fed by branches the hepatic artery while sparing healthy organs near the liver, or regions of the liver fed by other branches of the hepatic artery. The method entails deposition of membrane-covered wire frame structures in branches of the hepatic artery prior to deposition of radio-ablative particles such as Y90 microspheres.

We propose occluding extra-hepatic arteries with the embolic implant prior to radioembolization. The embolic implant can be used to occlude extra-hepatic arteries, such as the gastric, gastroduodenal and supraduodenal arteries, to make the current practice of occluding these arteries prior to radio-embolization faster and more certain. This can be done according to the method described below, by depositing a covered, wire frame embolic implant into the gastroduodenal and supraduodenal arteries or other branches of the hepatic artery proximal to the liver. The right gastric artery (pyloric artery) which usually branches off the proper hepatic artery, may also be occluded to protect the stomach, which it supplies. Murthy, et al., *Radioembolization of*

*Yttrium*-90 Microspheres for Hepatic Malignancy, Semin. Intervent. Radiol. 48 (March 2008).

We propose pre-embolization of extra-hepatic arteries, prior to deposition of radio-ablative particles, with the embolic implant described below. We also propose occluding the proper hepatic artery, distal to the gastroduodenal and supraduodenal arteries prior to deposition of radio-ablative particles in the hepatic artery or its branches. In this method, an occlusive device, such as the embolic implant described below, is deposited in the proper hepatic artery, distal to the branches serving organs other than the liver (the right gastric, gastric, gastroduodenal and supraduodenal arteries). After occlusion, the delivery catheter used to deliver the radio-ablative particles is slipped between the embolic implant and the hepatic artery wall, bypassing the embolic implant (deforming just enough to allow passage of the delivery catheter between the embolic implant and the artery wall), until the tip is distal to the embolic implant. With the delivery catheter disposed with its open tip in the hepatic artery distal to the embolic implant, radio-ablative particles are then delivered through the delivery catheter into the distal regions of the proper hepatic artery. With this method, retrograde flow of radio-ablative particles is prevented, but the extra-hepatic arteries are preserved and the current practice of occluding these arteries prior to radio-embolization obviated.

In another method, the embolic implants can be used to occlude the hepatic artery distal to the gastroduodenal and supraduodenal arteries, after deposition of radio-ablative particles, to make the current practice of occluding these arteries prior to radio-embolization unnecessary. Where retrograde flow is expected to be immediate and significant during the short time between deposition of the radio-ablative particles and deposit of the embolic implant, this method can be accomplished through a funnel catheter, or by using the embolic implant as a temporary measure, maintaining fixation with its delivery wire for a period adequate to stabilized the embolic particles within the distal regions of the proper hepatic artery and its hepatic branches.

We propose occluding deep branches of the hepatic artery, to leave un-diseased regions of the liver intact (and minimize reflux to other organs). This can be done according to the method described below, by depositing covered, wire-frame embolic implants into branches of the hepatic artery feeding healthy regions of the liver, while delivering radio-ablative particles into branches of the hepatic artery feeding diseased portions of the liver. This method may be useful where discrete regions of the liver are diseased while other regions are confirmed to be healthy.

The methods can be applied to the treatment of tumors and cysts elsewhere in the body, wherever diseased tissue can be treated with ablative substances deposited in feeder arteries, but reflux of the ablative substance to nearby arteries feeding healthy tissue or organs should be avoided.

BRIEF DESCRIPTION OF THE DRAWINGS

FIG. 15 illustrates an embolic implant with an oblong prolate wire-frame structure which is partially covered with a membrane.

FIG. 16 illustrates the several segments of the embolic implant.

DETAILED DESCRIPTION OF THE INVENTIONS

Figure 1:
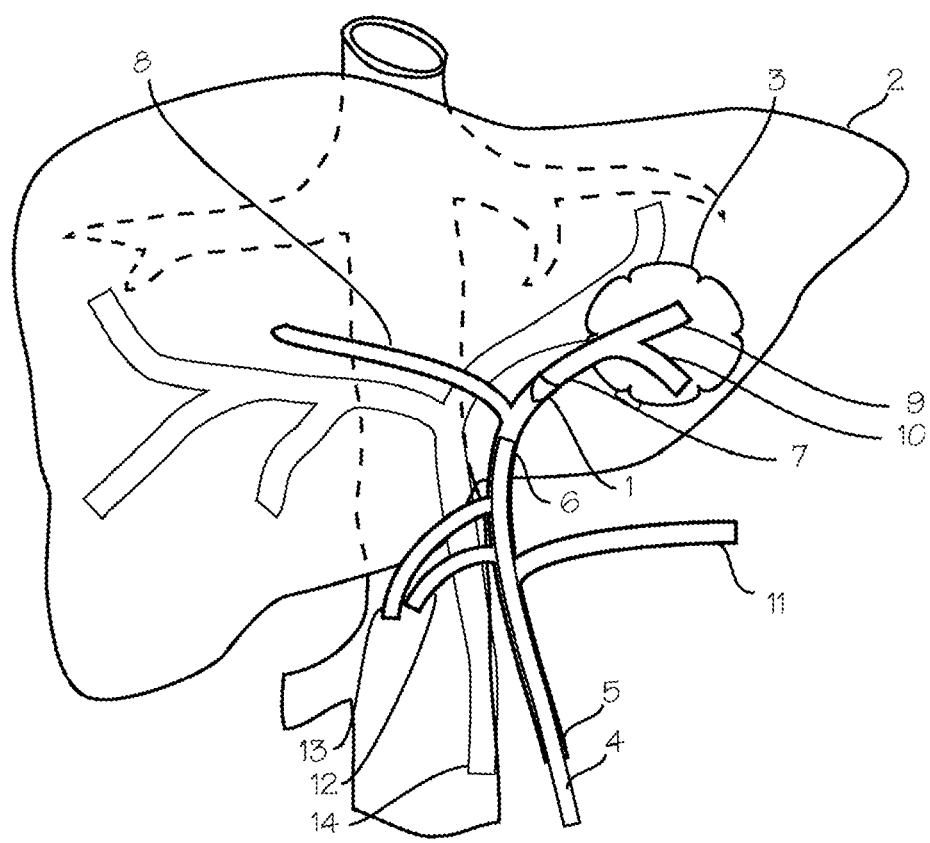
FIG. 1 illustrates the vasculature of the liver showing a potential placements of an embolic implant in conjunction with the deposition of radio-ablative particles.

FIG. 1 shows the vasculature of the liver in sufficient detail to illustrate the use of the embolic implants shown in the following illustrations. The embolic implant 1 is shown in an exemplary placement in the liver 2, which is diseased portion that includes a cancerous mass or tumor 3. The embolic implant is delivered to the vasculature serving the diseased portion of the liver with the delivery catheter 4. The hepatic vasculature, which is the intended environment of use for the embolic implant, supplies the liver with blood from the aorta and celiac trunk. The important arteries include the common hepatic artery 5 and proper hepatic artery 6 which supplies the left hepatic artery 7 and the right hepatic artery 8, or left and right branches of the proper hepatic artery. These arteries in turn supply the left lateral branch 9 and the left medial branch 10 of the left hepatic artery. The proper hepatic artery is the main artery supplying the liver with arterial blood. The proper hepatic artery and common hepatic artery refer to distal and proximal segments (respectively) of the hepatic artery. These arteries typically have an internal diameter of about 2 to 7 mm, most commonly from 3-5 mm. Extra-hepatic arteries, which branch off the hepatic artery or the proper hepatic artery, include the supraduodenal artery 11 which supplies the spleen (it is one of several extra-hepatic arteries), the gastric artery 12 which supplies a portion of the stomach, the gastroduodenal artery 13 which supplies a portion of the intestines. Each of these arteries are potential locations for deposition of an embolic implant which will prevent the unintended flow of radio-ablative particles into those arteries, and thus protect the issue served by those arteries from radio-ablation. The portal vein 14 and its branches (which serve as arteries in supplying the liver) are also depicted in FIG. 1, and the methods described herein can be applied to deposition of radio-ablative particles delivered in a laparoscopic procedure, but this is expected to be an unusual route for the procedure. (FIG. 1 shows a typical arrangement of hepatic vasculature. However, the hepatic vasculature can be highly variable from individual to individual, and all of the branches depicted (especially the left lateral branch) may not appear in all patients, and some patients may have addition branches, or branches corresponding to the branches illustrated but originating from elsewhere on the hepatic artery trunk or superior mesenteric artery.)

The radio-ablative particles may comprise various materials. Microspheres are currently the preferred delivery vehicle for Y90. The microspheres may be glass or resin, and are typically 20-60 microns in diameter. Other small particles capable of carrying Y90 or other suitable radioactive element can be used, including micelles, liposomes, macromolecules, vesicles, etc. Also, other radioactive elements are used for the procedure, such as Rhenium 188. (For the claims, we will refer to all such vehicles as radio-ablative particles.) Any radioactive particle, or bolus of radioactive particles may be used in the methods described herein. Radioembolic particles, which are both radioactive and act to create an embolism in the artery, may be used. Non-embolic radio-ablative particles may also be used. The particles may be incorporated in a matrix, microspheres, micelles, liposomes or other drug delivery vesicles. The particles need not be embolic, because the methods entail very quick occlusion of arteries that might be affected by the reflux of more free flowing particles or slurries.

The goal of hepatic radio-embolization is to kill cancerous cells within a cancerous mass or tumor within the liver by depositing a bolus of radio-ablative particles in the hepatic vasculature feeding the diseased region of the tumor in which the cancerous mass resided. In the procedure, a doctor or team of doctors, will perform the following steps:
1. Determines the location of a cancerous mass in the liver, usually by consulting x-rays, MMR or CAT-scan images previously prepared by a radiologist;
2. Determines the layout of the vasculature of the hepatic trunk, specifically identifying the location of the hepatic artery and its branches, and decides which branches may be occluded and which should be used for delivery of radio-ablative particles;
3. Inserts a catheter into the vasculature, typically through the femoral artery, navigating the tip of the catheter up through the femoral artery, to branch or branches selected for occlusion, and delivers an embolic implant through the catheter to the branch artery or arteries of the hepatic or extra-hepatic vasculature;
4. Inserts a second catheter through the vasculature (or uses the same catheter already in place in step 3), navigating the tip of the catheter to the branch or branches to be irradiated.
5. Delivers a bolus of radio-ablative particles in a slurry, into the branch or branches to be irradiated, through the catheter chosen for delivery of the radio-ablative particles.

Variations on the method are described in the following paragraphs.

Figure 2:
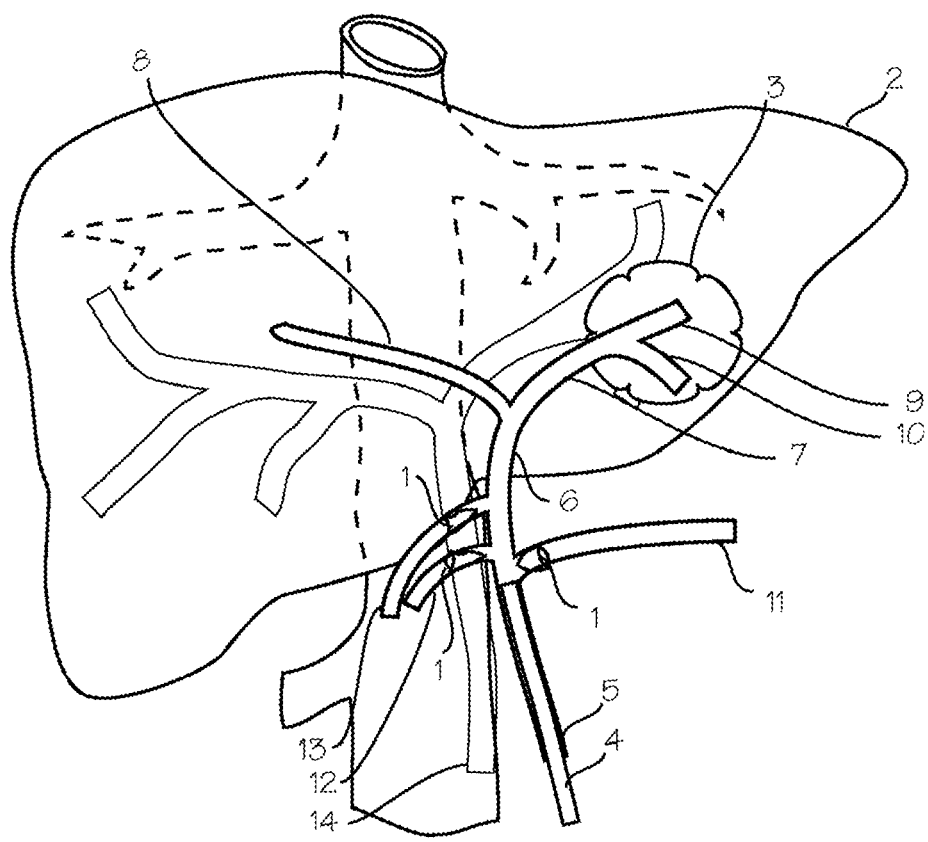
FIGS. 2, 3, and 4 illustrate a method of extra-hepatic embolization in conjunction with deposition of radio-ablative particles for radio-embolization.

FIG. 2 illustrates use of the embolic implant for pre-embolization of extra-hepatic arteries. In cases where the clinician decides that the entire hepatic arterial system should be radio-embolized with radio-ablative particles, the clinician may deliver radio-ablative particles to all the intra-hepatic branches of the proper hepatic artery (referring only those branch arteries of the proper hepatic artery that feed the liver). Prior to delivery of radio-ablative particles, the clinician will deposit an embolic implant described below into at least one extra-hepatic branch of the proper and/or common hepatic artery (for example, the supraduodenal artery, as illustrated in FIG. 2.) In other cases, the embolic implants can be used to occlude extra-hepatic arteries, such as the gastric or gastroduodenal arteries, to make the current practice of occluding these arteries prior to radio-embolization faster and more certain. This can be done according to the method described below, by depositing a covered, wire frame embolic implant into one or more extra-hepatic arteries (the gastric, gastroduodenal and supraduodenal arteries or other branches of the hepatic artery proximal to the liver). The right gastric artery (pyloric artery) which usually branches off the proper hepatic artery, may also be occluded to protect the stomach, which it supplies, as describe in Murthy. The method described in this paragraph is beneficial because retrograde flow of radio-ablative particles is prevented and pre-embolization is immediate. However, the extra-hepatic arteries are sacrificed and one embolic implant is needed for each extra-hepatic artery that is occluded.

Figure 3:
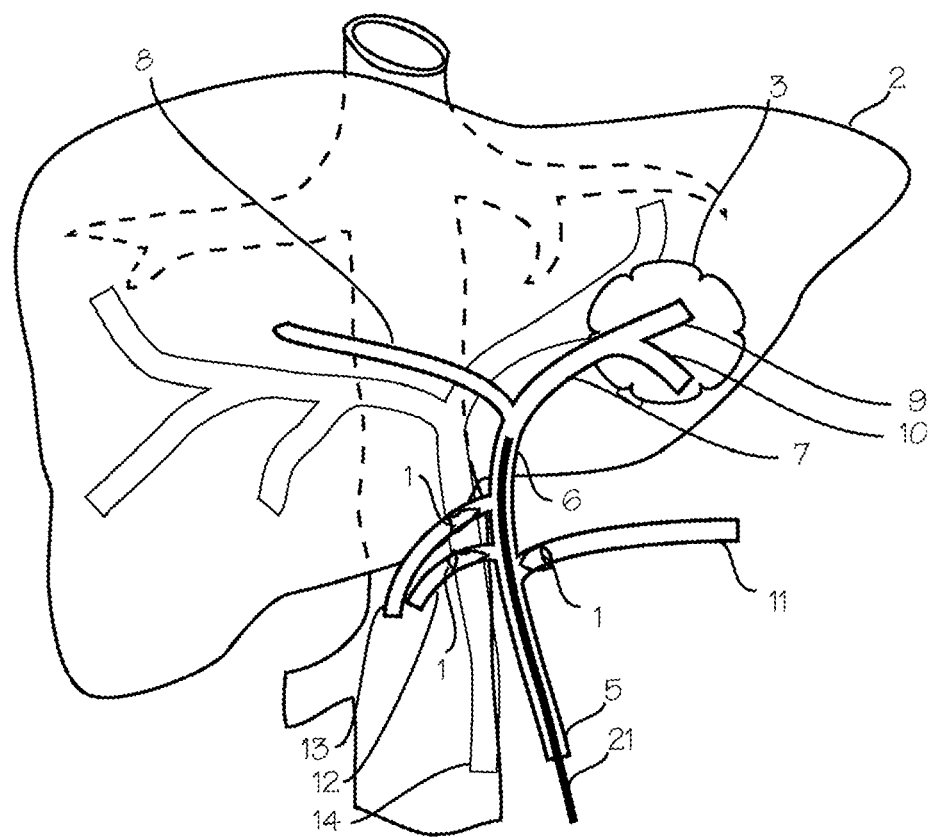
Figure 4:
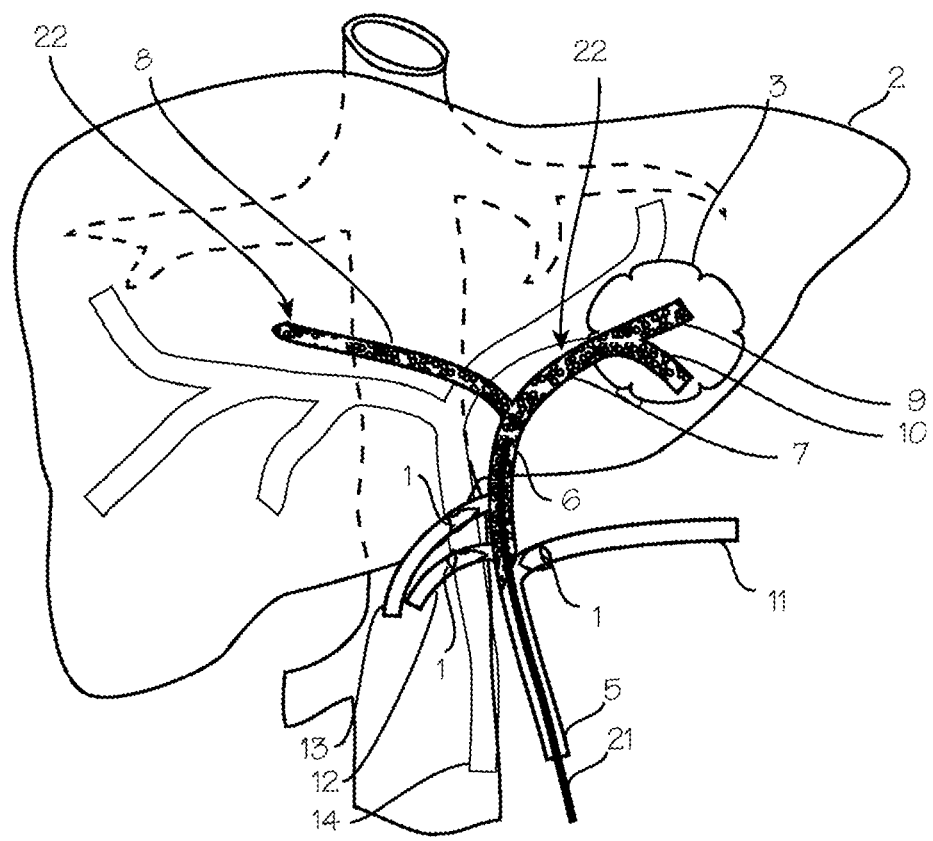

FIGS. 2, 3, and 4 illustrate a method of extra-hepatic embolization in conjunction with deposition of radio-ablative particles for radio-embolization. This method of pre-embolization is intended to protect extra-hepatic arteries from radio-ablation, with the drawback that a source of blood flow to those organs served by the occluded artery is sacrificed. Embolic implants 1 are shown disposed within the supraduodenal artery 11, gastric artery 12 and gastroduodenal artery 13 which supplies the spleen (these are extra-hepatic arteries). All extra-hepatic arteries may be occluded, but some may be left patent, depending on the clinician's determination of the need to occlude them. This method uses the embolic implant of FIGS. 15 and 16, which provides immediate occlusion, rather than the extended periods needed for occlusion using coils or Amplatzer® devices, which typical takes ten to fifteen minutes to stop blood flow which might carry refluxed radio-ablative particles into the extra-hepatic organs (in some cases, occlusion is never achieved). (Substantially complete occlusion typically is achieved with a few seconds of release from its delivery catheter. Absent deformity in the artery, substantially complete occlusion is quite certain to be achieved within five minutes or less, and occurs in 80% of cases in less than one minute. By substantially complete occlusion, we mean that either no blood flow is detectable on imaging, or any detectable blood flow is minimal such that little if any radio-ablative particles are expected to reflux past the embolic device.)

FIG. 2 shows an initial step in the procedure (which follows imaging of the liver to locate cancerous lesions, and, optionally, mapping of the proper hepatic artery and its branches). As shown in this illustration, the clinician has inserted a catheter 4 through the vasculature of the patient, into the proper hepatic artery, and into an extra-hepatic artery which branches off the hepatic artery, such as the supraduodenal artery 11. Through this catheter, the clinician has delivered an embolic implant 1 into the supraduodenal artery 11. The catheter 4 used to deliver embolic device may then be withdrawn, or left in place to serve as a guide for the next catheter to be used. The implant is deposited as close to the junction between the supraduodenal artery and the proper hepatic artery as is feasible, to prevent as much reflux as possible. (The clinician might also occlude other extra-hepatic arteries, such as the gastric artery 12 gastroduodenal artery 13.) As shown in FIG. 3, the clinician next navigates a second catheter 21 into the proper hepatic artery, preferably downstream of the occluded hepatic artery (or arteries). As shown in FIG. 4, the clinician next injects radio-ablative particles through the second catheter, into the proper hepatic artery, so that these particles are delivered to all the hepatic branches of the proper hepatic artery. The radio-ablative particles are injected in a bolus 22 which becomes lodged in the arteries feeding diseased portion of the liver. The embolic implant in the supraduodenal artery prevents the reflux of the radio-ablative particles into the supraduodenal artery, and thus into the spleen. The second catheter is removed after deposition of the radio-ablative bolus. The embolic implant is left in the occluded artery.

Figure 5:
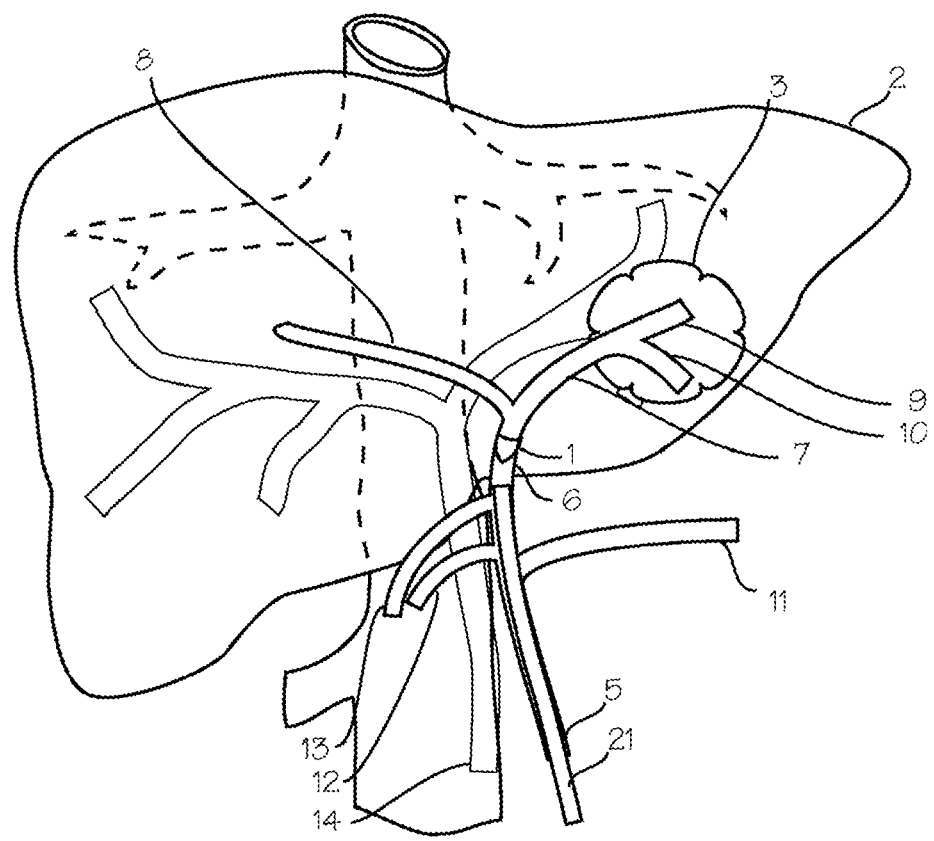
FIGS. 5, 6, 7, and 8 illustrate a method of embolization of the proper hepatic artery in conjunction with deposition of radio-ablative particles for radio-embolization.
Figure 6:
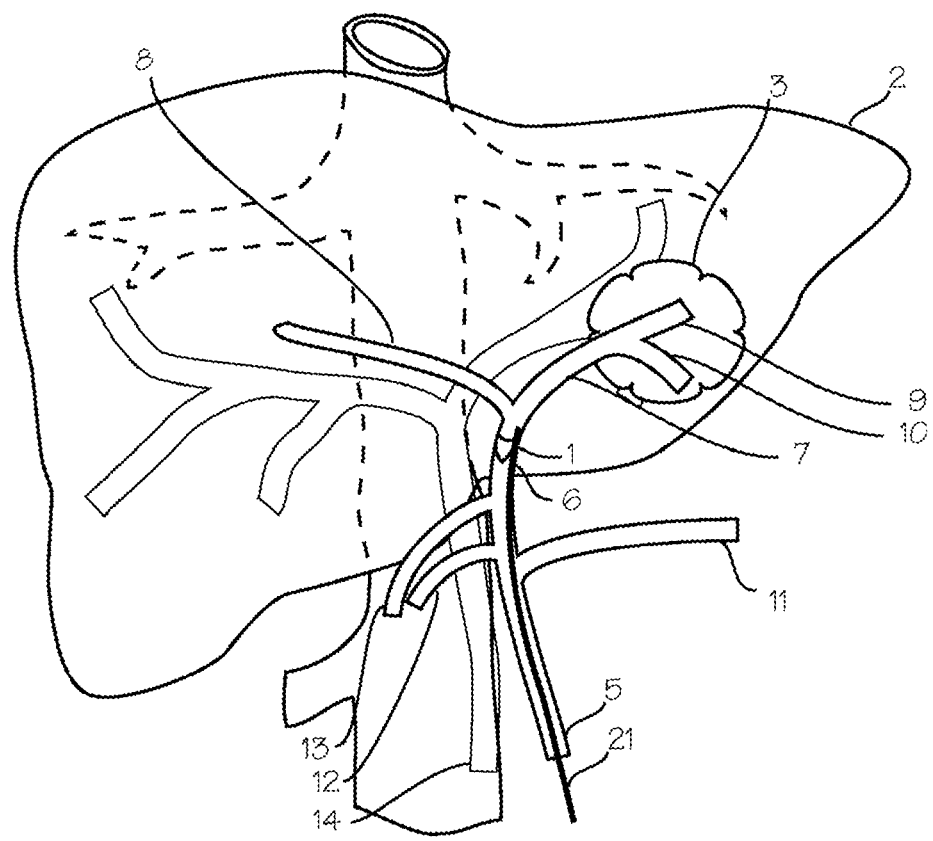
Figure 7:
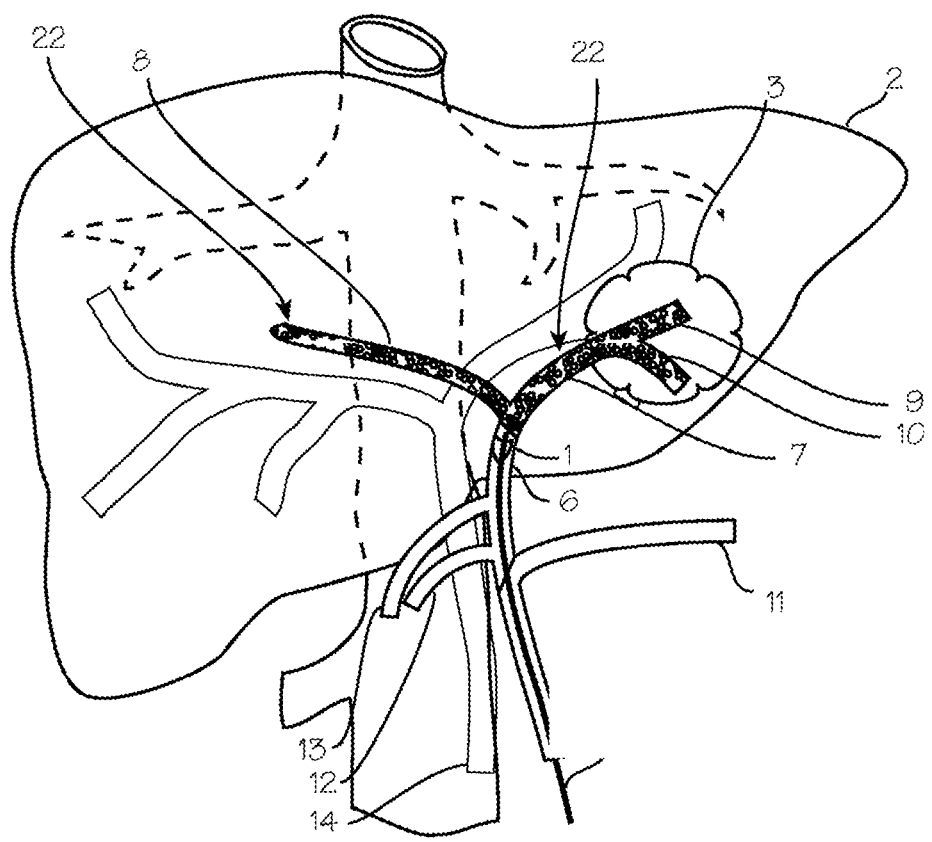
Figure 8:
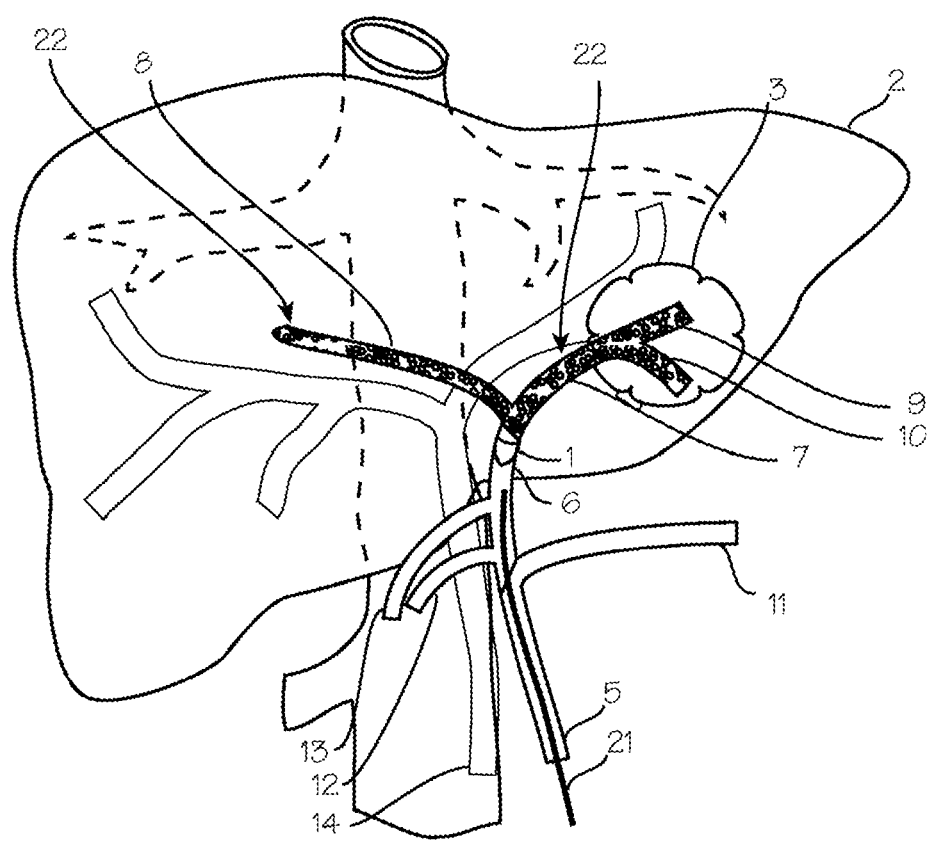

The radio-embolization procedure can be performed by depositing radio-ablative particles in the hepatic artery, or a branch of the hepatic artery, after placement of the embolic implant immediately proximal to the bolus, without occluding other branch arteries, such as the extra-hepatic arteries. FIGS. 5, 6, 7, and 8 illustrate this method of embolization of the proper hepatic artery in conjunction with deposition of radio-ablative particles for radio-embolization. As shown, the embolic implant is used to occlude the proper hepatic artery distal to the gastroduodenal and supraduodenal arteries, BEFORE deposition of radio-ablative particles in the proper hepatic artery and all its branches. (The embolic implant may be released from its delivery wire for permanent placement, or retained on its delivery wire for removal shortly after delivery of the radio-ablative particles). This isolates the bolus from non-target blood vessels. After placement of the embolic implant, the clinician navigates a second catheter into the proper hepatic artery, passing the embolic implant. This makes the current practice of occluding extra-hepatic arteries prior to radio-embolization unnecessary. To accomplish this method, the clinician performs the following steps:

1. The clinician deposits the embolic implant in the proper hepatic artery 6 distal to the extra-hepatic arteries, using delivery catheter 4, as shown in FIG. 5;
2. The clinician navigates a catheter 21 into the proper hepatic artery 6, and pushes the tip of the catheter past or beyond the embolic implant 1, deforming the embolic implant 1 as necessary, until the opening at the distal end of the catheter is distal to the embolic implant 1, as shown in FIG. 6;
3. The clinician delivers a bolus 22 of the radio-ablative particles through the catheter, into the proper hepatic artery or its branches, with the embolic implant 1 in place, at a location distal to the embolic implant 1, as shown in FIG. 7;
4. The clinician withdraws the catheter and leaves the embolic implant 1 permanently implanted, as shown in FIG. 8. (Optionally, the embolic implant 1 can be removed after the bolus of radio-ablative particles embolizes and sets up to the point where it will not reflux significantly.)

Figure 9:
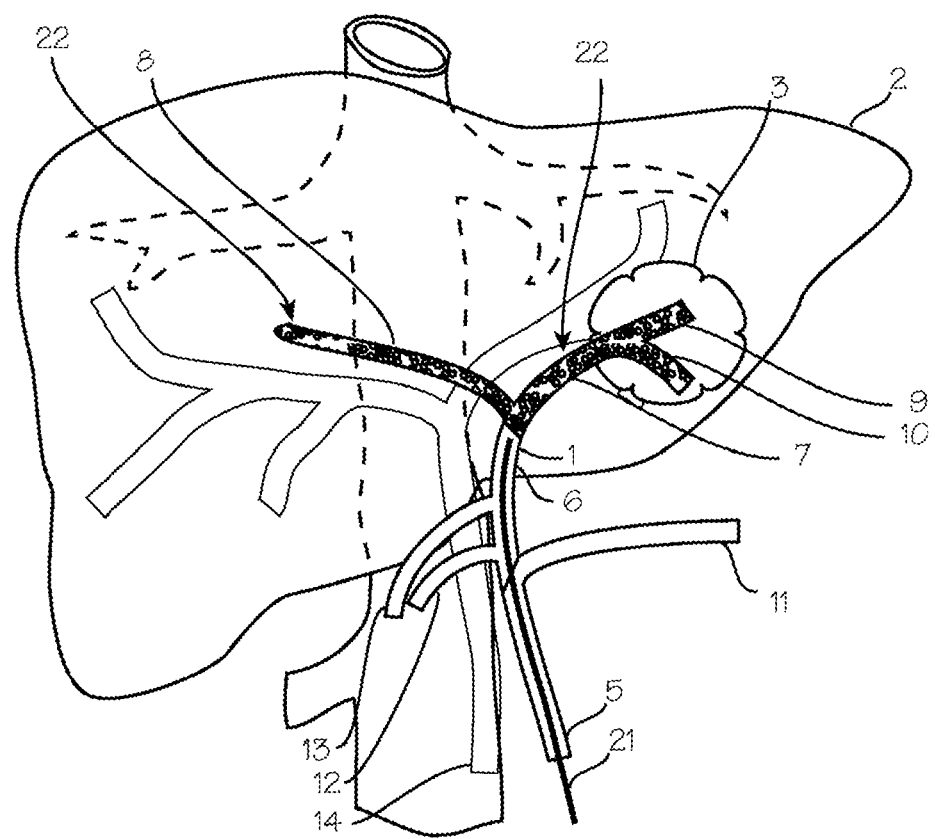
FIGS. 9, 10, 11, and 12 illustrate a method of embolization of the proper hepatic artery in conjunction with deposition of radio-ablative particles for radio-embolization.
Figure 10:
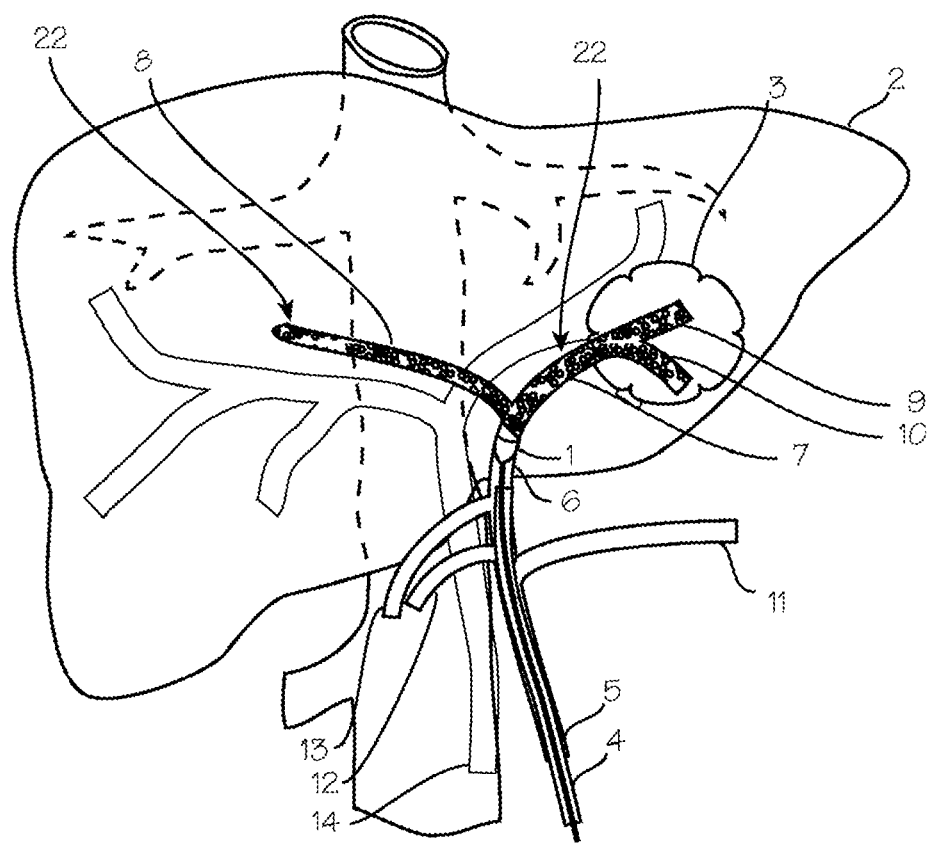
Figure 11:
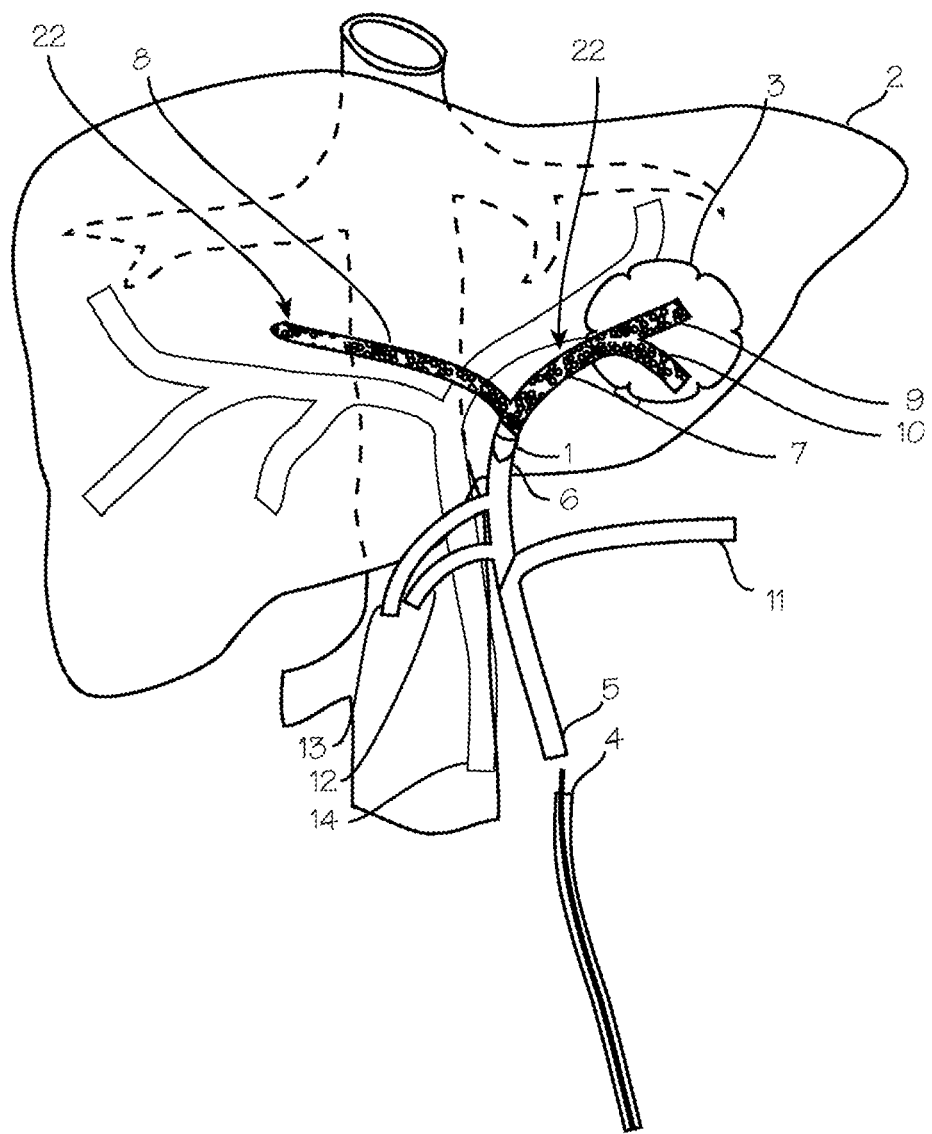
Figure 12:
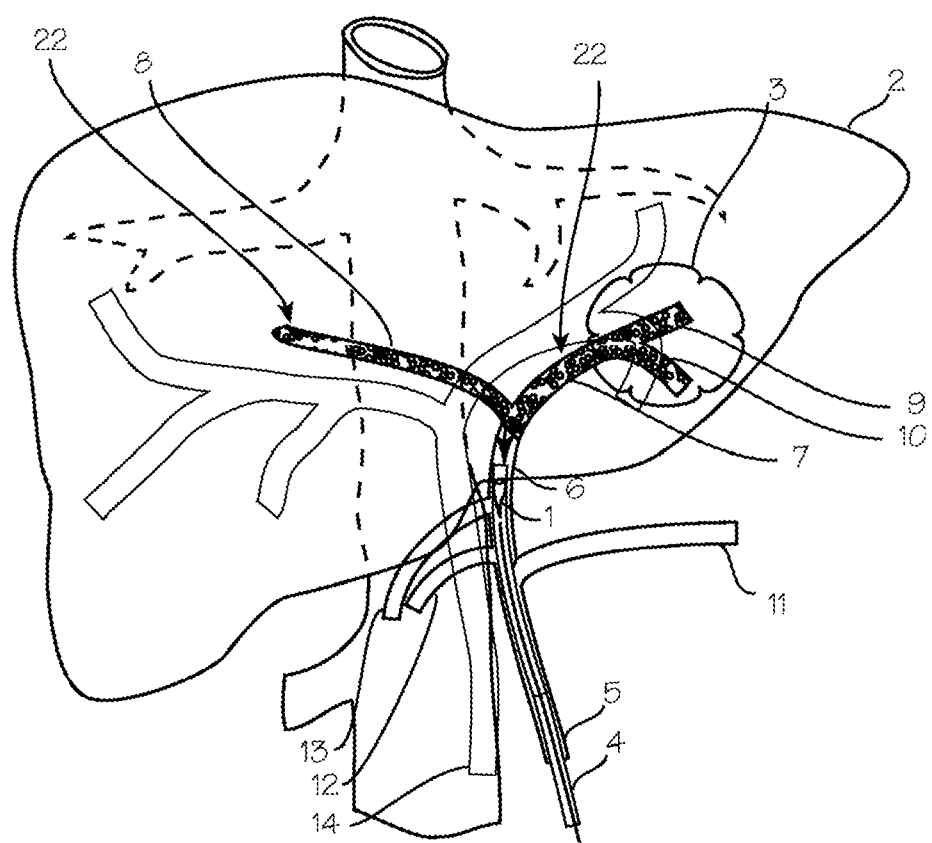

The radio-embolization procedure can be performed by depositing radio-ablative particles in the hepatic artery, or a branch of the hepatic artery, followed by placement of the embolic implant immediately proximal to the bolus, without occluding other branch arteries. This is illustrated in FIG. 9, which illustrates that the clinician has deposited a bolus 22 of radio-ablative particles into the proper hepatic artery and its branches without first placing an embolic device in the proper hepatic artery, its branches, or extra-hepatic branches. As shown in FIG. 10, the embolic implant may be used to occlude the proper hepatic artery distal to the gastroduodenal and supraduodenal arteries, and is deposited with catheter 4 after deposition of radio-ablative particles in the proper hepatic artery or its branches. As shown in FIG. 11, the embolic implant is released from its delivery wire for permanent placement, and the catheter is removed. (Alternatively, the catheter may be retained on its delivery wire for removal shortly after delivery of the radio-ablative particles are secured in place by thrombosis of the blood in the artery). This isolates the bolus from non-target blood vessels. This method also makes the current practice of occluding extra-hepatic arteries prior to radio-embolization unnecessary. Optionally, as shown in FIG. 12, the embolic implant 1 can be removed along with the delivery catheter 4. This step can be accomplished where the radio-ablative particles and the slurry used to delivery them are non-embolic, and permit healing and revascularization of the diseased liver tissue after radio-ablation.

The radio-embolization procedure can be performed by depositing radio-ablative particles in the hepatic artery, or a branch of the hepatic artery, followed by placement of the embolic implant immediately proximal to the bolus, without occluding other branch arteries. For example, the embolic implant may be used to occlude the proper hepatic artery distal to the gastroduodenal and supraduodenal arteries, after deposition of radio-ablative particles in the proper hepatic artery and all its branches. This isolates the bolus from non-target blood vessels. Though some particles may reflux in the time between deposition of the bolus and deposition of the embolic implant, the various branch arteries will be preserved. This makes the current practice of occluding these arteries prior to radio-embolization unnecessary.

Figure 13:
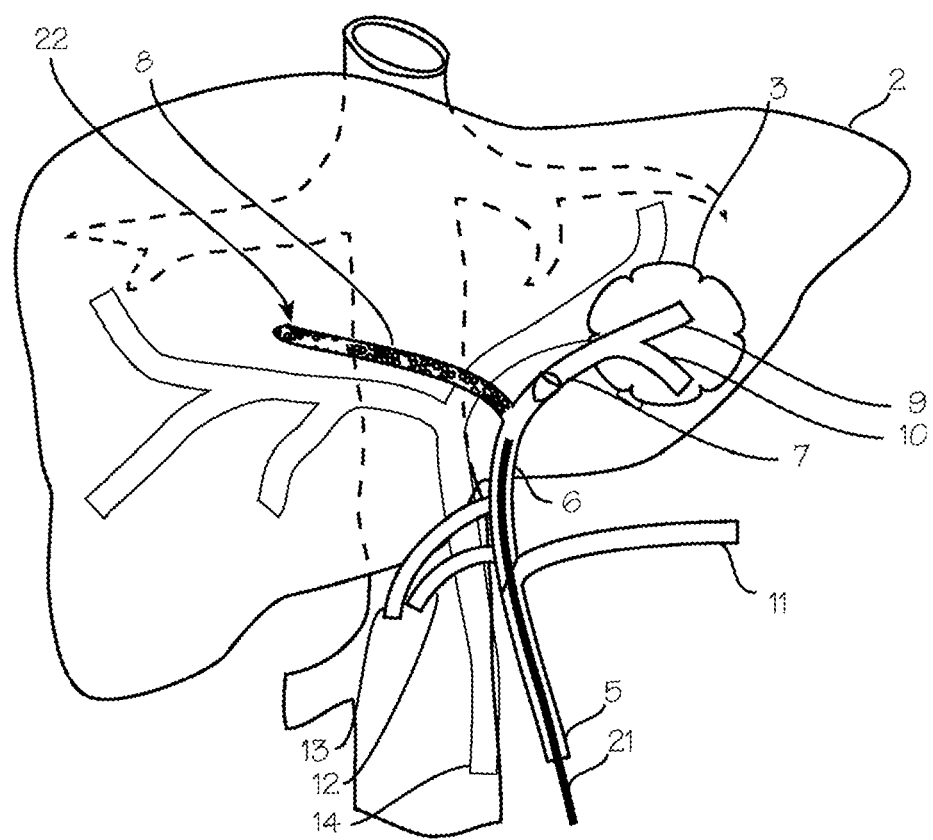
FIG. 13 illustrates a method of embolization of the hepatic artery branches in conjunction with deposition of radio-ablative particles for radio-embolization.

FIG. 13 is schematic diagram of the vascular of the liver illustrating location for deposition of radio-ablative particles deep within distal region of the hepatic branches. In FIG. 13, the insertion catheter 4 and an embolic implant 1 are shown threaded through the proper hepatic artery 6 and the left hepatic artery 7, with the embolic implant disposed within the left hepatic artery 6, proximal to (upstream of) the lateral and medial branches 9 and 10. As shown in this Figure, a bolus of radio-ablative particles is deposited in the right hepatic artery 8 artery, after the left hepatic artery 7 has been occluded. With the left hepatic artery 7 occluded, the radio-ablative particles cannot migrate or reflux out of the right hepatic artery 8 into the occluded branch to injure areas of the liver previously served by the left hepatic artery 7. Though the left hepatic artery 7 is occluded, the region of the liver served by this branch is also served by branches of the portal vein and may soon be revascularized by new arteries and capillaries branching off the remaining portions of the hepatic artery and its branches. In this procedure, branches of the hepatic artery are occluded prior to delivery of the radio-ablative particles, and are delivered to branches that feed healthy regions of the liver that are not to be ablated. In an alternative to this procedure, an embolic implant can be delivered after the radio-ablative particles are deposited, and may be placed immediately upstream of the bolus, in the same branch as the bolus (in the illustration, in the right hepatic artery 8), to trap the radio-ablative particles in place and prevent reflux.

As illustrated in FIG. 13, the method of radio-embolization entails the several steps recited above, and occluding at least one branch of the proper hepatic artery, or more specifically at least one branch of the left or right hepatic arteries, with a covered wire frame embolic implant described below, followed by delivery of a bolus of radio-ablative particles suitable for radio-ablation into the other branch of the proper hepatic artery. For example, prior to delivery of radio-ablative particles to the right hepatic artery, a clinician will deliver an embolic implant into the left hepatic artery. Under this method, the region of the liver supplied by the right hepatic artery will be ablated, while the region of the liver supplied by left hepatic artery will be spared. Similarly, prior to delivery of radio-ablative particles to the first branch of the left hepatic artery, a clinician will deliver an embolic implant into the second branch of the left hepatic artery. Under this method, the region of the liver supplied by the first branch of the left hepatic artery will be ablated, while the region of the liver supplied by second branch of the left hepatic artery will be spared. The particular hepatic artery to be occluded and the particular hepatic artery to which radio-ablative particles are delivered will depend on the location of the tumor or mass to be treated and the particular vascular arrangement of the patient. (The embolic implant may be deposited in non-target branches after deposition of the radio-ablative particles in the target branches, though this risks some reflux.)

In many patients, the hepatic artery arrangement differs from what is depicted as typical anatomy. In some patients, the right hepatic artery can branch off of the superior mesenteric artery, and/or the left hepatic artery can branch off the left gastric artery. In many patients, there is no proper hepatic artery, and the common hepatic artery is trifurcated directly into the right hepatic artery, left hepatic artery and gastroduodenal artery. In such cases, the clinician may choose to implant an embolic implant in both the right hepatic artery and left hepatic artery followed by, or preceded by, deposition of radio-ablative particles in the right hepatic artery and left hepatic artery.

Figure 14:
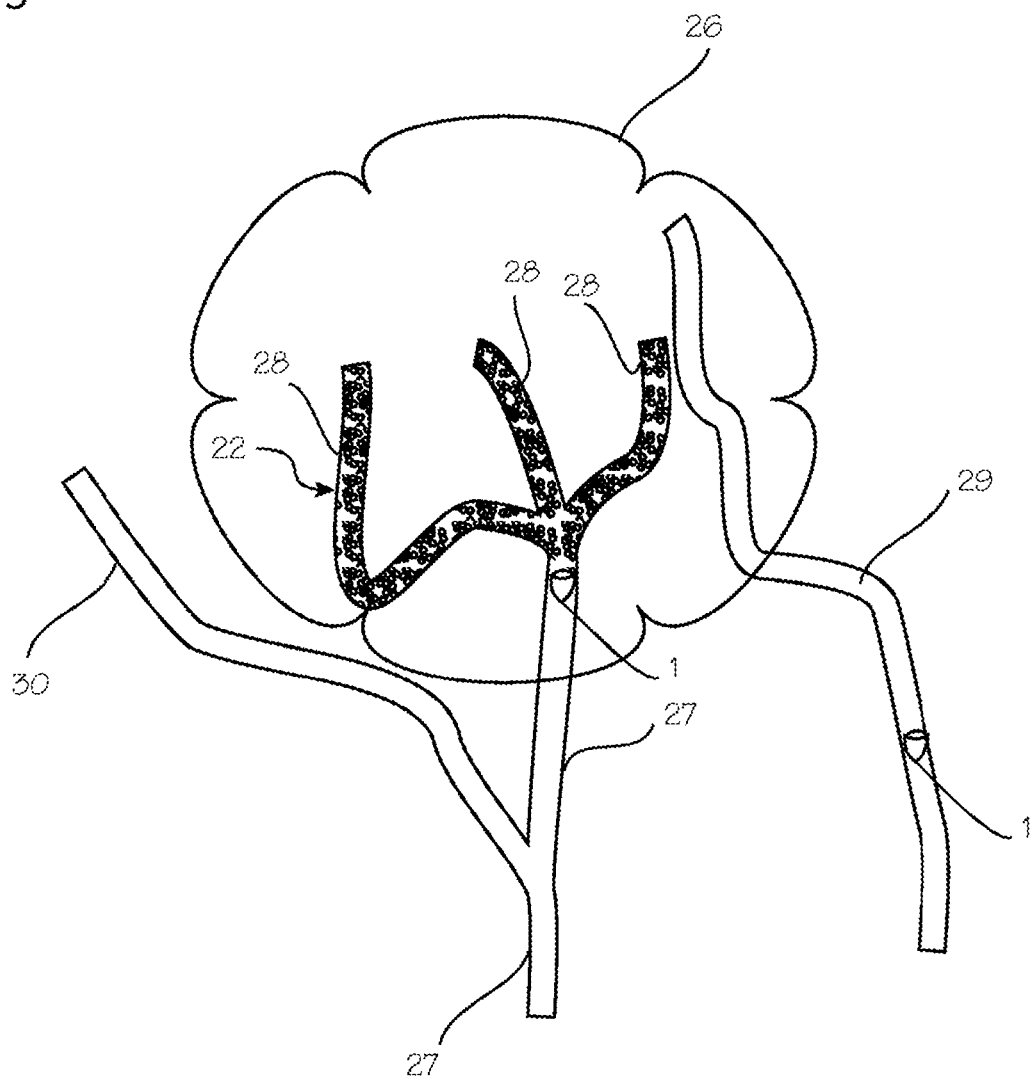
FIG. 14 illustrates a method of embolization of an artery or branches in conjunction with deposition of radio-ablative particles for radio-embolization of a tumor or cyst.

FIG. 14 illustrates a method of embolization of an artery or branches in conjunction with deposition of radioembolic particles for radio-embolization of a tumor, cyst, or other diseased region of tissue, which may be located anywhere in the body. It may be a discrete tumor, a benign neoplasm (such as a uterine fibroid) or a malignant neoplasm. As shown in FIG. 14, a tumor 26 is fed by a main artery 27 with several branch arteries 28 and, in some cases, an accessory artery 29. A branch of the main artery, item 30, supplies blood to healthy tissue near the tumor. Each of the methods described above for treating the liver, with embolic devices in conjunction with radio-ablative particles, can be used to ablate the tumor. For example, as illustrated, an embolic implant 1 is deposited in the main feeder artery 27, either before or after deposition of bolus of radio-ablative particles 22. Also, another embolic implant 1 may be implanted in the accessory artery to ensure that all major sources of blood flow to the tumor are blocked. The bolus of radio-ablative particles is deposited in the artery or arteries feeding the tumor, either after placement of the embolic implant (according to the method of FIGS. 5 through 8) or before placement of the embolic implant (according to the method of FIGS. 9 through 12).

FIG. 15 illustrates an embolic implant, or parent artery occlusion device, suitable for use in the hepatic vasculature of a patient. The embolic implant 31 is wire-frame structure with an overall tubular shape, with struts converging to the longitudinal center (the long axis) of the device where they are bound together with rings. The wire frame structure is partially covered with a membrane. The wire-frame structure is formed by laser-cutting a nitinol tube. The resultant segments of the wire-frame structure include a first zig-zag segment 32 and a second zig-zag segment 33, with V-shaped elements 34 joined at the "open" end of the V, through small longitudinal struts 35. These struts are longitudinally offset from each other, so that the embolic implant can be compressed into a small diameter configuration in which the struts and the junctions between the zig-zag segments can be compressed to smaller diameter than would be possible if the struts were longitudinally aligned. The struts can be compressed into a diameter smaller than the original tube from which the device is cut. Each zig-zag segment is characterized by vertices 36 of each V-shaped element which point longitudinally away from the longitudinal center of the device. From the vertices of the V-shaped elements, end struts 37 extend longitudinally away from the longitudinal center of the device, and curve inwardly toward the radial center of the device. The proximal serpentine struts continue into a segment of straight struts 38 (see FIG. 16). The distal serpentine struts continue into a segment of straight struts 47 (see FIG. 16). (These struts may be serpentine, as depicted, or straight.) The ends of the end struts furthest from the longitudinal center are secured in small rings 39 and 40. (The rings are made of a radiopaque material, such as gold, platinum alloys, etc., to help facilitate placement of the embolic implant under fluoroscopic guidance.) The device can be characterized by a proximal end 41 and a distal end 42, defined in reference to the delivery catheter used to implant the device, and the pathway along which the implant is navigated to reach the implant site. At the proximal end, the wire frame structure is joined to a delivery rod 43 through a detachment joint 44. The detachment joint can be a screw thread attachment joint or electrolytic detachment joint (any detachment means, including those described below, may be used to hold the embolic implant during delivery and detach it from the delivery rod.)

FIG. 16 illustrates the wire frame structure, as if unrolled, to illustrate its several segments. The first and second zig-zag segments 32 and 33 are connected through small central struts 35. The circumferential line marked as item 45 is shown to illustrate the longitudinal displacement of the struts relative to each other. Because the struts and the V vertices are not aligned along the same circumferential line, the implant can be compacted without being limited by interfering contact of the struts. The serpentine struts extending longitudinally from the zig-zag segments connect to scrap zig-zag segments 46. These segments are formed during the laser cutting process, and are used to facilitate gathering of the serpentine struts into the rings at either end of the device. After the serpentine struts are secured in the rings, these portions are removed and discarded. As indicated in FIG. 16, the central zig-zag segments are joined together to form several diamond shaped cells with longitudinally displaced vertices, referring both to the longitudinally pointing vertices and the circumferential vertices. The combined zig-zag segments span 0.180" along the longitudinal axis of the device. The serpentine struts span 0.230".

The wire-frame structure is preferably made of superelastic alloy, formulated to be superelastic at body temperature, such that the implant is self-expanding upon release from its delivery catheter. It may also be made of resilient metals or polymers, or shape memory alloy or shape memory polymers. The zig-zag segments are illustrated with sharply defined V-shaped elements, which assists in compacting the device. The V-shaped elements can be replaced with U-shaped elements, or sinusoidally curved elements, to create serpentine segments which are joined together and the serpentine struts joined to the bottom of the U-shaped elements.

Referring again to FIG. 15, the wire-frame structure of the embolic implant is covered with a membrane 48. The membrane 48 covers the proximal end of the embolic implant, from the ring 40 to the longitudinal center of the implant, and, as illustrated, extending over both zig-zag segments. The membrane is made of ePTFE and is glued to the metal struts of the wire-frame structure with suitable adhesive. This membrane is impermeable to blood on the proximal facing surface 49, and may also be impermeable on the circumferential surface which covers the center of the device. The membrane is secured to the wire frame structure such that blood is substantially prevented from flowing through the implant or the artery when embolic implant is deployed in the artery.

The membrane, as illustrated, is made of two 0.0003" (0.00762 mm) thick sheets of ePTFE with a layer of adhesive, such as Bacon Adhesive 430 or 431, sandwiched between the two ePTFE sheets such that the ePTFE is impregnated with the adhesive. The membrane material is prepared by applying the adhesive to one sheet, and scraping or pressing the adhesive away, leaving the sheet wetted with a thin layer of adhesive on the surface of the sheet and leaving adhesive impressed into the pores of the ePTFE. The second sheet is then disposed over the wetted surface, that this assembly is then scraped and pressed to flatten the assembly. The result is a sheet of ePTFE which can be glued to the metal struts of the wire-frame structure, despite the normal resistance of ePTFE to adhesion. Tantalum powder may be mixed into the adhesive to provide some degree of radiopacity to the completed membrane. The sheet is then formed into the roughly conical shape shown, stretched over a conical mandrel, and heated then peeled off the mandrel. It is then glued or otherwise affixed to the expanded wire-frame structure. The membrane can also be formed of a single layer of ePTFE which is stretched and heat-formed to match the outer circumference of the expanded wire-frame structure.

The embolic implant may be fashioned so that it opens to a fully expanded, unrestrained diameter of 5 mm at its center, but can be compacted to a diameter of less than 1 mm, and preferably to a diameter of about 0.5 mm to fit in a delivery catheter with an internal diameter of 0.021" (0.5334 mm) or less and outer diameter of 0.039" (1 mm) (3 F) or less.

The embolic implant may instead be fashioned so that it opens to a fully expanded, unrestrained diameter of 6.5 mm at its center, but can be compacted to a diameter of less than 1 mm, and preferably to a diameter of about 0.63 mm to fit in a delivery catheter with an internal diameter of 0.027" (0.6858 mm) or less and outer diameter of 0.039" (1 mm) (3 F) or less.

The embolic implant can be coated to enhance thrombogenicity or space-filling characteristics within its structure. Coatings can include hydrophilic hydrogel or expandable foam which is applied to the implant 100 and dried prior to use. Upon exposure to blood or other liquid, the hydrogel or foam absorbs water and swells in volume. Such volume swelling can increase the hydrogel or foam layer thickness up to ten times, or more. The hydrophilic hydrogel can comprise fibrin glue, prothrombin, or other blood clotting substance. Thrombogenic (blood clotting) chemicals can be applied to the embolic implant with or without the hydrogel.

In use, a clinician (a vascular clinician, interventional radiologist, etc.) inserts the embolic implant, packed in a delivery catheter, to a segment of the branch of the hepatic artery targeted for pre-embolization. This will typically be accomplished through a guide catheter, which the clinician will insert prior to inserting the delivery catheter. After confirming the location of the device (under fluoroscopy), the clinician withdraws the delivery catheter to expose and release the embolic implant. The embolic implant may be drawn back into the delivery catheter and repositioned if necessary (via the delivery wire). When the embolic implant is properly positioned and deployed from the delivery catheter, the clinician disconnects the embolic implant from the delivery wire. Depending on the detachment mechanism, the clinician may twist the delivery wire to disconnect a screw-thread connector, or operate a small power supply to deliver electric current through a conductor running from the detachment joint to the power supply (the pushrod may serve as the conductor) to melt or electrolytically sever the joint and detach the embolic implant from the pushrod.

Because the radio-embolization particles are intended to result in embolization of the target branch artery, if embolization takes place quickly (again, with a conveniently short intra-operative time frame) the embolic implant may be retained on the delivery wire while the radio-ablative particles are deposited, and removed after the bolus of radio-ablative particles has set up (clotted with surrounding blood in the artery) and is no longer subject to retrograde flow or reflux. Also, the branch arteries may be temporarily occluded, with the embolic implant deposited in a non-target artery prior to particle delivery, held in place while the bolus of radio-ablative particles is delivered and while it is setting up and clotting with surrounding blood, and the embolic implant may be removed after the bolus is no longer subject to retrograde flow or reflux. This technique can be facilitated by delivery of thrombogenic agents (thrombin, fibrin glue, etc.) into the bolus, after the bolus has been taken up by the target artery.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method comprising:
    implanting an embolic implant in vasculature of a patient at a site proximal to a diseased region of tissue within the patient, wherein the diseased region is proximate healthy tissue or organs, and wherein the diseased region is supplied with blood through a main artery of the vasculature, and the healthy tissue or organs is supplied with blood through a branch artery of the main artery, the embolic implant comprising a wire-frame structure and a membrane covering at least one end of the wire-frame structure, wherein the membrane substantially blocks blood from flowing through the at least one end of the wire-frame structure in a direction of blood flow through the vasculature when the implant is deployed in the vasculature; and
    depositing an ablative substance in the main artery distal to the embolic implant site.

2. The method of claim 1, wherein implanting the embolic implant in the vasculature comprises implanting the embolic implant in the branch artery before depositing the ablative substance, wherein substantially complete occlusion of the branch artery and substantially complete stoppage of blood flow in the branch artery is achieved in less than 5 minutes from implantation of the embolic implant in the branch artery.

3. The method of claim 1, wherein implanting the embolic implant in the vasculature comprises implanting the embolic implant in the branch artery after depositing the ablative substance.

4. The method of claim 1, wherein implanting the embolic implant in the vasculature comprises implanting the embolic implant in the main artery, distal to the branch artery, before depositing the ablative substance, the method further comprising:
    navigating a catheter into the main artery, and navigating a distal segment of the catheter past the embolic implant;
    delivering the ablative substance through the catheter to deposit the ablative substance distal to the embolic implant; and
    withdrawing the catheter from the main artery.

5. The method of claim 4, further comprising removing the embolic implant from the main artery after deposition of the ablative substance.

6. The method of claim 1, wherein implanting the embolic implant in the vasculature comprises implanting the embolic implant in the main artery, distal to the branch artery, after depositing the ablative substance.

7. The method of claim 1, wherein the ablative substance comprises microspheres, liposomes, macromolecules, or vesicles.

8. The method of claim 1, wherein the ablative substance comprises a radioactive element.

9. The method of claim 1, wherein the ablative substance is a radioembolic sub stance.

10. The method of claim 1, wherein the ablative substance is a non-embolic radio-ablative substance.

11. The method of claim 1, wherein the wire-frame structure comprises:
a pair of opposing zigzag segments including a plurality of V-shaped elements defining an open end, the V-shaped elements joined at the open end of the V-shaped elements, the V-shaped elements defining proximal or distal vertices pointing proximally or distally away from a center of the wire-frame structure; and
a plurality of longitudinally oriented struts extending from the proximally or distally pointing vertices of the V-shaped elements, the longitudinally oriented struts being joined together near a radial center of the wire-frame structure at one end of the embolic implant, wherein the wire-frame structure is formed of a self-expanding material.

12. The method of claim 1, wherein the embolic implant includes a proximal end and a distal end, the wire-frame structure comprising:
a pair of opposing zigzag segments including a plurality of V-shaped elements defining an open end, the V-shaped elements joined at the open end of the V-shaped elements via short longitudinally aligned struts to form a central portion of the wire-frame structure, the short struts being longitudinally displaced from each other, the V-shaped elements defining proximal or distal vertices pointing proximally or distally away from a center of the wire-frame structure;
a plurality of longitudinally oriented struts extending from the proximally pointing vertices of the V-shaped elements, the longitudinally oriented struts being joined together near a radial center of the wire-frame structure at the proximal end of the embolic implant, wherein the wire-frame structure is formed of a self-expanding material; and
the membrane disposed over the proximal end of the embolic implant, the membrane having a proximal facing surface, the membrane being impermeable to blood on the proximal facing surface.

13. A method for radio-ablative treatment of a liver of a patient, the method comprising:
implanting an embolic implant in vasculature of the patient at a site proximal to the liver of the patient, wherein the liver is proximate at least one other organ, wherein the liver is supplied with blood through a hepatic artery of the vasculature, and the at least one other organ is supplied with blood through an extra-hepatic branch artery of the hepatic artery, the embolic implant comprising a wire-frame structure and a membrane covering at least one end of the wire-frame structure, wherein the membrane substantially blocks blood from flowing through the at least one end of the wire-frame structure in a direction of blood flow through the vasculature when the embolic implant is deployed in the vasculature; and
depositing an ablative substance in the hepatic artery distal to the embolic implant site.

14. The method of claim 13, wherein implanting the embolic implant in the vasculature comprises implanting the embolic implant in the extra-hepatic branch artery before depositing the ablative substance, wherein substantially complete occlusion of the extra-hepatic branch artery and substantially complete stoppage of blood flow in the extra-hepatic branch artery, is achieved in less than 5 minutes from implantation of the embolic implant in the extra-hepatic branch artery.

15. The method of claim 13, wherein implanting the embolic implant in the vasculature comprises implanting the embolic implant in the extra-hepatic branch artery after depositing the ablative substance.

16. The method of claim 13, wherein implanting the embolic implant in the vasculature comprises implanting the embolic implant in the hepatic artery, distal to the extra-hepatic branch artery, before depositing the ablative substance, the method further comprising:
navigating a catheter into the hepatic artery, and navigating a distal segment of the catheter past the embolic implant;
delivering the ablative substance through the catheter to deposit the ablative substance distal to the embolic implant; and
withdrawing the catheter from the hepatic artery.

17. The method of claim 13, wherein implanting the embolic implant in the vasculature comprises implanting the embolic implant in the hepatic artery, distal to the extra-hepatic branch artery after depositing the ablative substance.

18. The method of claim 13, wherein the ablative substance comprises a radioactive element.

19. The method of claim 13, wherein the ablative substance is a radioembolic sub stance.

20. The method of claim 13, wherein the ablative substance is a non-embolic radio-ablative substance.

21. The method of claim 13, wherein the wire-frame structure comprises:
a pair of opposing zigzag segments including a plurality of V-shaped elements defining an open end, the V-shaped elements joined at the open end of the V-shaped elements, the V-shaped elements defining proximal or distal vertices pointing proximally or distally away from a center of the wire-frame structure; and
a plurality of longitudinally oriented struts extending from the proximally or distally pointing vertices of the V-shaped elements, the longitudinally oriented struts being joined together near a radial center of the wire-frame structure at one end of the embolic implant, wherein the wire-frame structure is formed of a self-expanding material.

22. The method of claim 13, wherein the embolic implant includes a proximal end and a distal end, the wire-frame structure comprising:
a pair of opposing zigzag segments including a plurality of V-shaped elements defining an open end, the V-shaped elements joined at the open end of the V-shaped elements via short longitudinally aligned struts to form a central portion of the wire-frame structure, the short struts being longitudinally displaced from each other, the V-shaped elements defining proximal or distal vertices pointing proximally or distally away from a center of the wire-frame structure;

a plurality of longitudinally oriented struts extending from the proximally pointing vertices of the shaped elements, the longitudinally oriented struts being joined together near a radial center of the wire-frame structure at the proximal end of the embolic implant, wherein the wire-frame structure is formed of a self-expanding material; and the membrane disposed over the proximal end of the embolic implant, the membrane having a proximal facing surface, the membrane being impermeable to blood on the proximal facing surface.

* * * * *